Figure 1:
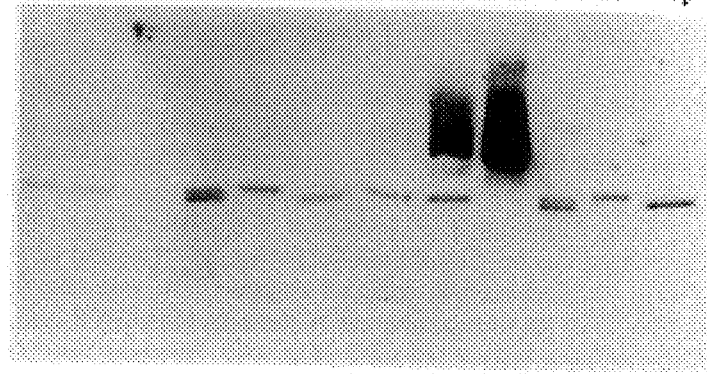
Figure 2A:
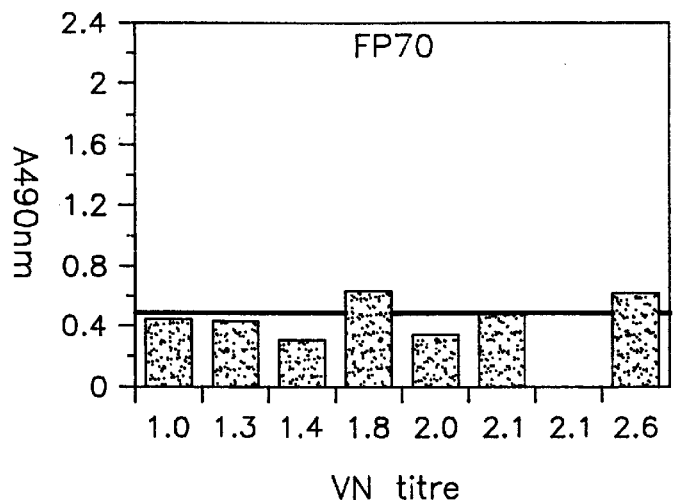
Figure 2B:
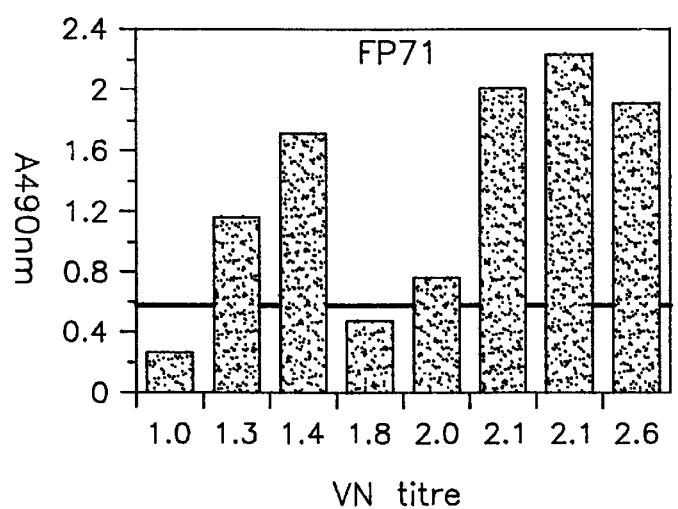
Figure 2C:
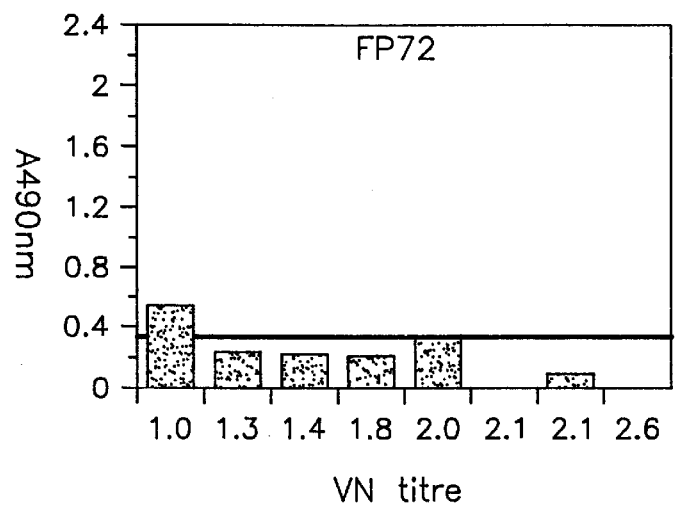
Figure 2D:
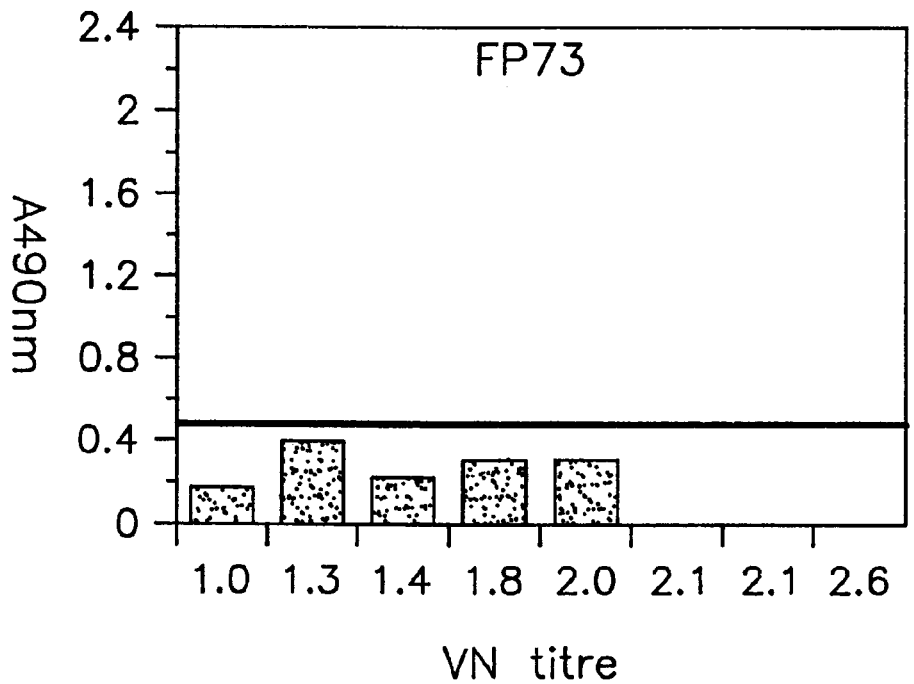
Figure 2E:
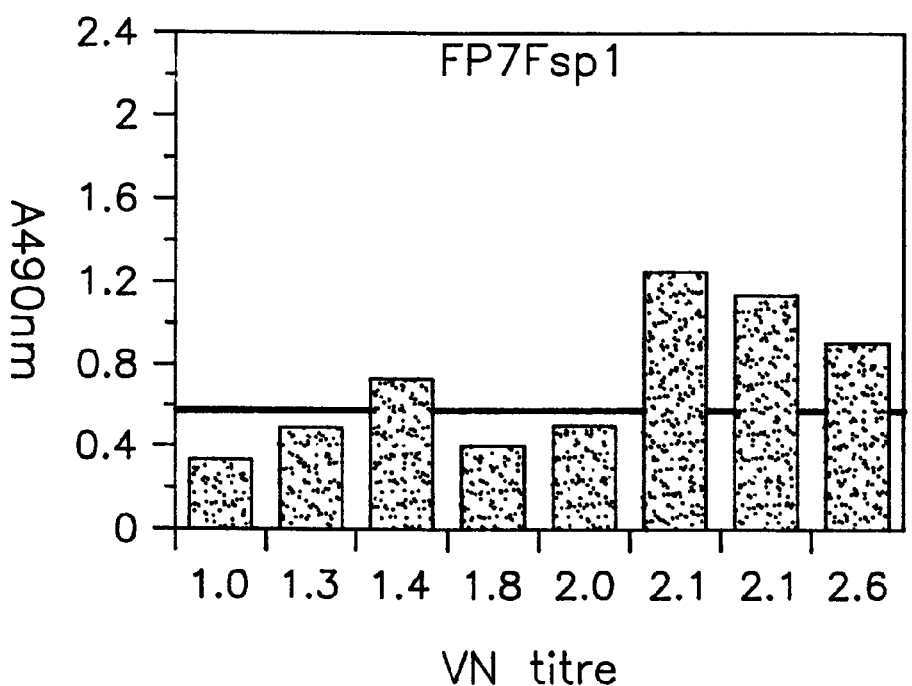

United States Patent [19]
Chirnside

[11] Patent Number: 6,090,390
[45] Date of Patent: Jul. 18, 2000

[54] DIAGNOSTIC TEST FOR EQUINE ARTERITIS VIRUS MEDIATED DISEASE

[75] Inventor: Ewan Douglas Chirnside, Suffolk, United Kingdom

[73] Assignee: Animal Health Trust, Suffolk, United Kingdom

[21] Appl. No.: 08/981,459

[22] PCT Filed: Jun. 20, 1996

[86] PCT No.: PCT/GB96/01505

§ 371 Date: Feb. 19, 1998

§ 102(e) Date: Feb. 19, 1998

[87] PCT Pub. No.: WO97/00963

PCT Pub. Date: Jan. 9, 1997

[30] Foreign Application Priority Data

Jun. 20, 1995 [GB] United Kingdom .................. 9512464

[51] Int. Cl.[7] .......................... A61K 39/12; A61K 39/21; A61K 39/38; A61K 39/385
[52] U.S. Cl. ..................... 424/204.1; 424/207.1; 424/184.1; 424/186.1; 424/193.1; 424/196.11; 530/326
[58] Field of Search .............................. 424/204.1, 184.1, 424/186.1, 193.1, 196.11, 207.1; 530/324

[56] References Cited

U.S. PATENT DOCUMENTS 3,590,127  6/1971  Bryans et al. ............................. 424/89
5,202,430  4/1993  Brian et al. ........................... 536/23.72

FOREIGN PATENT DOCUMENTS

WO95/19438  7/1995  WIPO.

OTHER PUBLICATIONS

De Vries, et al.: Structrural proteins of Equine arteritis virus: J. Vir.: pp. 6294–6303, Nov. 1992.
Chirnside: Equine Arteritis Virus:an overview: Brit. Vet. J. : 148(3): pp. 181–197, 1992.
Den Boon, et al. :Equine arteritis virus is not . . .: J. Vir. : vol. 65 (6): pp. 2910–2920, Jun. 1991.
De Vries, et al.: Structural proteins of equine arteritis virus: J. Vir. : vol. 66 (11): pp. 6294–6303, Nov. 1992.
Harlow, et al. : Antibodies a laboratory manual: pp. 151 and 553–569, 1988.
Journal Gen Virology, Jun. 1994, Chirnside et al, pp. 1491–1497 "Comparison of M and N gene Sequences distinguishes . . . ".
Journal Gen Virology, Jun. 1991, Den Boon Ja et al, pp. 2910–2920, "Equine arteritis virus is not a togavirus but belongs . . . ".
Nucleic Acids Res, Jun. 11, 1990, De Vries AA et al, pp. 3241–3247, "All subgenomic mRNAs of equine arterities virus . . .".
Journal Gen Virology, Nov. 1992, De Vries AA et al, pp. 6294–6303, "Structural proteins of equine arteritis virus".
Rev Sci Tech, Sep. 1994, Zientara, pp. 845–854, "Equine infectious arteritis: molecular biology, epidemiology . . . ".
Bristish Vet Journal, 1992, pp. 148, 181–197, Chirnside; "Equine Arteritis Virus—An Overview".
Virus Research, 1995, pp. 277–288, Chirnside et al, "Expression Cloning and Antigenic Analysis of the Nucleocapsid Protein . . .".
Journal Gen Virology, Aug. 1995, pp. 1989–1998, Chirnside et al "Equine arteritis virus–neutralizing antibody in the horse . . .".

*Primary Examiner*—Jeffrey Strucker
*Assistant Examiner*—Brett Nelson
*Attorney, Agent, or Firm*—Jacobson, Price, Holman & Stern, PLLC

[57] ABSTRACT

This invention relates to recombinant DNA and polypeptides encoded thereby which have use in the provision of vaccines, diagnostic test kits and methods of diagnosis and treatment or prophylaxis for equine arteritis virus (EAV) and EAV mediated disease.

14 Claims, 3 Drawing Sheets

DIAGNOSTIC TEST FOR EQUINE ARTERITIS VIRUS MEDIATED DISEASE

This application is a 371 of PCT/GB76/01505 filed Jun. 20, 1996.

The present invention relates to recombinant DNA and polypeptides encoded thereby, having use in provision of antibodies, vaccines, diagnostic test kits and methods of diagnosis and treatment or prophylaxis for equine arteritis virus (EAV) and equine arteritis virus mediated disease.

Equine viral arteritis, a disease for which equids are the only reported hosts, has been known for some 40 years and manifests itself with widely varying clinical signs. In its most severe form EAV infection causes abortion and foal death which makes it a potentially significant commercial threat to, inter alia, the horse breeding industry. Early veterinary articles refer to it as epizootic cellulitis, pinkeye or equine influenza. Disease outbreaks are identified infrequently and field isolates of the single stranded RNA virus itself are rare.

EAV is transmitted by the respiratory and venereal routes, with a 30–60% carrier state existing in seropositive stallions which persistently shed virus in their semen. Thus the venereal route is a particular cause for concern, as these shedding stallions may infect broodmares at mating. In the light of the potential economic importance of the virus and its stud carrier mediated infection capability there exists a requirement for prophylactic treatment and reliable diagnosis of equine viral arteritis, and rapid identification of equids previously exposed to the infectious agent. Laboratory tests based on ELISA using whole virus as antigen, virus neutralisation (VN) and complement fixation (CF) formats have been developed (see Chirnside (1992) Br Vet J 148, pp 181). The known ELISA is relatively sensitive when applied to tissues, eg sera, from horses previously vaccinated for other diseases such as influenza and herpesvirus, while the VN and CF formats have limited temporal sensitivity; the VN test is unable to distinguish between vaccination and natural infection.

Vaccination procedures have concentrated on safety and efficacy of whole inactivated virus and attenuated live virus vaccines. The live vaccine can induce short term shedding of virus from the nasopharynx and does not prevent this causing infection of commonly housed animals which have not been so treated. It is not yet known if formalinised vaccines or other inactivated vaccine preparations provide reliable protection.

Attempts to provide improvements to both diagnostic tests and vaccines have included studies into panels of antibodies raised against various EAV proteins. A 29K envelope protein ($G_L$) has been identified as antigenic (Balasuriya et al, (1993) J Gen Virol 74, 2525–2529; Deregt et al, (1994) J Gen Virol 75, 2439–2444) and peptides derived from this protein induce a virus neutralising response in horses (Chirnside et al, (1995) J Gen Virol in press). A previous invention (UK Patent Application No GB 9400656.4) provided isolated peptides of $G_L$ that produce a potent neutralising immune response against EAV when administered to animals, particularly horses, and these peptides provided sensitive detection of EAV antibodies when used as binding agents in biding assays formats. Further provided was DNA encoding for these peptides.

In the first aspect of the present invention there is provided a method for testing for the presence of antibodies to equine arteritis virus comprising use of a peptide or peptide conjugate of the viral nucleocapsid (N) protein as a specific binding agent. Such test is preferably of ELISA format but may use the peptide or conjugate as immobilised binding agent or labelled secondary binding agent in a so-called sandwich assay. Preferred peptides or peptide conjugates of the invention comprise epitopes present in the amino acid sequence corresponding to amino acids 1 to 110 (SEQ ID No.2) of EAV N, more preferably amino acids 1 to 69 of EAV N (SEQ ID No.3) and, additionally, amino acids 1 to 28 (SEQ ID No.4), or a sequence having at least 90% homology to these sequences. These peptides are antigenic and may be used to provide isolated antibodies produced by an immunological response when a suitable host is exposed to the antigen.

In a binding assay where the peptide or peptide conjugate is immobilised this method may conveniently be carried out by use of commercially available assay plates onto which the peptide or conjugate is coated by suitable incubation in the known manner. For the purpose of assay, a sample to be screened for EAV antibodies, eg a serum sample, is typically incubated in contact with the plate, eg in the wells, whereafter any EAV antibody present is identified by exposure to eg an anti-horse IgA, IgM, IgG or other immunoglobulin conjugated to a reporter group. Such reporter group may be in the form of radiolabel, chemical label or a biological label. A typical biological label is an enzyme or cofactor, eg biocin, and is detected by exposure to all the reactants necessary for a reporter reaction to occur dependent upon the presence of the reporter group. In the case of biotin the well may be exposed to screptavidin-peroxidase and the substrate o-phenylenediamine dihydrochloride and the absorbance of the plate determined at 490 nm.

In a further example, an immobilised anti-horse IgA, IgM, IgG or ocher immunoglobulin antibody raised in another animal, may be used to bind a specific class of horse antibody; the immobilised horse antibody provided may then be exposed to a solution containing labelled peptide or conjugate of the invention whereby the presence of anti-EAV antibody is indicated by assay of the amount of label present. Other assay formats such as competitive assays using either bound or unbound peptide or conjugate will occur to those skilled in the art; these will include simple observation of agglutination between peptide or conjugate and the antibody in a simple dilution test.

In a further aspect of the present invention there are provided test kits for use in carrying out the assay of the invention characterised in that they comprise a peptide, peptide-conjugate or antibodies of the invention, together with optional agents and items necessary for performing such assays. Such agents and items may include other binding agents or color forming agents such as labelled antibodies eg biotinylated anti-horse IgG, horseradish peroxidase, streptavidin peroxidase conjugate and o-phenylenediamine dihydrochloride. It will be realised that the term peptide and peptide conjugate as used herein will encompass oligopeptides, polypeptides and proteins as long as they fulfill the criteria of the invention with regard to the immunological activity and content of epitopic sequences. The term conjugate designates conjugation to any physiologically acceptable entity.

The peptides, peptide conjugates and binding assays of the present invention will now be described, by way of example only, by reference to the following sequence listing, figures and examples.

SEQUENCE LISTING

SEQ ID NO: 1: is the DNA sequence equivalent to the entire EAV genome minus the first 18 bases and the polyA tail.

SEQ ID NO: 2: is the amino acid sequence of the virus nucleocapsid protein (N) encoded by open reading frame (ORF) 7, and that is fused in-frame to GST in FP70 to express rN1-110.

SEQ ID NO: 3: is the amino acid sequence corresponding to amino acids 1 to 69 of the EAV N protein, and that is fused in-frame to GST in FP71 to empress rN1-69.

SEQ ID NO: 4.: is the amino acid sequence corresponding to amino acids 1 to 28 of the EAV N protein, and that is fused in-frame to GST in FP7Fspl to express rN1-28.

FIGURES

FIG. 1 shows an immunoblot of purified fusion proteins (Fps 70, 71, 72, 73 and 7Fspl) and glutathione-S-cransferase (Gst) with serum grom an individual horse pre- and post-EAV infection. For plasmid and fusion protein derivations see Table 1.

FIG. 2 shows equine sera ELISA absorbance values to recombinant EAV N proteins. ELISA plates were coated with 0.5 µg per well of purified fusion protein (FP) or glutathione-S-transferase (GST). Sera were tested in two replicate wells to each antigen and the absorbance of each well read at 490 nm. The GST absorbance was subtracted from the FP absorbance to derive an EAV-specific value. Each bar represents the mean value from two replicates of each serum. Cut-off points determining ELISA seropositivity for each antigen, calculated from the absorbance values of 8 VN- control sera are shown as a horizontal line on each graph: FP70=0.592; FP71=0.483; FP72=0.294; FP73=0.407; FP7Fsp1=0.582. The virus neutralising titre (VN titre) of the 8 sera tested are shown on the x-axis as $\log_{10}$ VN titres.

EXAMPLE 1

Production of peptides and conjugates of the invention and DNA and vectors encoding therefore.

cDNA encompassing EAV open reading frame (ORF) 7 (den Boon et al [1991], J Virol, 65, 2910–2920; de Vries et al, [1992], J Virol 66, 6294–6303) corresponding to the EAV N protein was cloned into the bacterial vectors pGEX-3X and pGEX-2T (Table 1) and constructs screened for fusion protein expression using PAGE with cloning confirmed by RE digestion analysis and sequencing over the plasmid/insert junctions. Plasmids are referred to as FPx, the expressed recombinant fusion proteins as rNy-z (where y and z refer to amino acid residue numbers in EAV N). Affinity purified glutathione-S-transferase (GST) fusion proteins were screened for reactivity in immunoblots with a panel of pre- and post-EAV-infection equine sera. Although horse sera exhibit some background absorbance to GST in immunoblots, post-infection sera bound strongly and specifically to fusion proteins containing amino acids N1-110 and N1-69, and failed to bind fusion proteins containing NI-28, N70-89 and N90-110 specifically (FIG. 1).

EXAMPLE 2

ELISA using EAV nucleocapsid (N) fusion proteins

Dynatech Immulon 3 microtitre plates were coated with rN1-69 or rN1-28 antigen by exposure to 100 µl of 5µg/ml antigen in 0.05 M carbonate buffer at pH9.6 (Sigma cat No C3041) at 4° C. overnight.

Plates were washed three times with phosphate buffered saline (PBS) containing 0.05% Tween 3 20 (PBST) and then blocked with 100l PBST containing 5% normal goat serum (Seralab) (PBSTG) for 1 hour at 37° C. Plates were washed again three times with PBST to render them ready for use.

Test sera were diluted 1:100 in PBSTG and 100 µl of this solution added to wells prepared as above and incubated for 90 minutes at 37° C. Plates were washed again three times with PBST and solution prepared by diluting goat anti-horse IgG biotin conjugate (KPL catalogue No 162102) 1:1000 in PBSTG and adding 1001 to each well before being incubated for 90 minutes at 37° C. Plates were washed three times with PEST and a solution prepared by diluting streptavidin-peroxidase conjugate (KPL catalogue No 143000) 1:1000 in PBSTG and adding 100 µl to each well before incubating at room temperature for 30 minutes. Plates were washed three times with PBST and 100 µl O-phenylenediamine dihydrochloride (Sigma cat. No P8287) (0.5 mg/ml in 0.05 phosphate citrate buffer, pH5.0, Sigma cat. No. P4922)) added to each well and incubated for 10 minutes at room temperature. 50 µl 4M $H_2SO_4$ was added to stop the reaction and absorbence read at 490 nm. Since horse sera at a 1:100 dilution can bind native GST it is necessary to subtract absorbance readings obtained for sera against GST from the GST-fusion protein absorbence. Each serum is tested in duplicate wells against each is antigen.

FIG. 2 shows the results of 8 VN equine sera in ELISA to different recombinant EAV N proteins. Cut-off points determining ELISA seropositivity for each antigen, calculated from the value of 8VN negative equine sera, are shown as a horizontal line on each graph (rN1-110=0.592; rN1-69= 0.483; rN70-89=0.294; rN90-110=0.407; rN1-28=0.582). From these results rN1-69 and rN1-28 were identified as suitable antigens for the detection of EAV-specific antibodies in ELISA.

EXAMPLE 3

ELISA using rN1-69 and rN1-28 binding agents

Panels containing seronegative and virus neutralising sera were tested in ELISA to purified rN1-69 and rN1-28 (Table 2). In ELISAs a recombinant fusion protein containing residues 1-69 or 1-28 discriminated between pre- and post-infection equine sera. In additional ELISA tests screening pre- and post-EAV vaccination samples and including isolate specific sera, the rNI-69 and rN1-28 antigens were able to discriminate between samples pre- and post vaccination with Artervac (commercial inactivated virus vaccine), even in the absence of vaccination induced neutralising antibody, and detect isolate-specific VN sera as seropositive in ELISA. The mean absorbence rising following vaccination were 1.240+0.690 and 0.495+0.352 for rN1-69 and rN1-28 respectively.

TABLE 1

Nucleocapsid gene constructs and fusion proteins

| Plasmid (FP) | Amino acid residue (N) | Fusion protein (rN) | Fusion protein size (kDa) | EAV cDNA clone | Restriction digest | pGEX vector restriction digest |
|---|---|---|---|---|---|---|
| 70 | $-3^1$–110 | 1–110 | 42 | $106^2$ | HindIII (12305) - HindIII$^v$ (>12700) | 3X x HindIII |
| 71 | $-3^1$–69 | 1–69 | 36 | FP70 | HindIII (12305) - RsaI (12523) | 3X x BamhI EcoRI$^K$ |
| 72 | 70–89 | 70–89 | 30 | FP70 | RsaI (12524) - RsaI (12583) | 2T x SmaI |
| 73 | 90–10 | 90–110 | 30 | FP70 | RsaI (12584) - EcoRI$^v$ (.12700) | 2T x SmaI |

TABLE 1-continued

Nucleocapsid gene constructs and fusion proteins

| Plasmid (FP) | Amino acid residue (N) | Fusion protein (rN) | Fusion protein size (kDa) | EAV cDNA clone | Restriction digest | pGEX vector restriction digest |
|---|---|---|---|---|---|---|
| 7Fsp1 | $-3^1$–28 | 1–28 | 31 | $106^2$ | HindIII$^k$ (12305) - FspI (12399) | 3X x SmaI |

$^k$ 3' recessed end filled in with the Klenow fragment of DNA polymerase
$^v$ Vector derived
$^1$ The negative number corresponds to additional amino acids cloned into pGEX which are not encoded by ORF 7
$^2$ see de Vries et al 1990, Nuclei Acids Research 18, 3241–3247.

TABLE 2

Comparison of virus neutralising antibody titres and ELISA absorbence values

| Equine sera | Log$_{10}$ VN antibody titre$^1$ | VN test result | rN1-69 ELISA A$_{490}$ | rN1-69 ELISA result$^b$ | rN1-28 ELISA A$_{490}$ | rN1-28 ELISA result$^c$ |
|---|---|---|---|---|---|---|
| Negative controls | | | | | | |
| 32277 | 0 | − | 0.126 | − | 0.170 | − |
| 32278 | 0 | − | 0.156 | − | 0.310 | + |
| 32779 | 0 | − | 0.098 | − | 0.180 | − |
| 32280 | 0 | − | 0.095 | − | 0.101 | − |
| 32281 | 0 | − | 0.115 | − | 0.155 | − |
| 32282 | 0 | − | 0.115 | − | 0.134 | − |
| 32283 | 0 | − | 0.161 | − | 0.204 | − |
| 32284 | 0 | − | 0.152 | − | 0.222 | − |
| Post infection | | | | | | |
| 32252 | 3.6 | − | 3.746 | + | 2.250 | + |
| 32255 | 2.475 | + | 2.504 | − | 0.679 | + |
| 32257 | 2.625 | + | 3.660 | + | 1.856 | + |
| 32258 | 2.700 | + | 3.520 | + | 1.182 | + |
| 32259 | 2.550 | + | 2.536 | + | 0.650 | + |
| 32260 | 2.850 | + | 1.238 | − | 0.314 | + |
| 32261 | 1.875 | + | 2.753 | + | 2.024 | + |
| 32262 | 2.475 | + | 3.00 | + | 0.920 | + |
| Paired vaccination samples | | | | | | |
| 33745 pre | 0 | − | 0.132 | − | 0.230 | − |
| post | 0.3 | − | 0.664 | + | 0.340 | + |
| 33746 pre | 0 | − | 0.353 | + | 0.344 | + |
| post | 0.45 | − | 0.967 | + | 0.580 | + |
| 33747 pre | 0 | − | 0.168 | − | 0.256 | − |
| post | 0.525 | − | 2.427 | + | 1.212 | + |
| 33962 pre | 0 | − | 0.157 | − | 0.170 | − |
| post | 0 | − | 0.884 | + | 0.387 | + |
| 33963 pre | 0 | − | 0.117 | − | 0.145 | − |
| post | 0.9 | + | 2.144 | + | 0.997 | + |
| 33964 pre | 0 | − | 0.156 | − | 0.175 | − |
| post | 0 | − | 1.572 | + | 0.851 | + |
| 33435 pre | 0 | − | 0.348 | + | 0.286 | − |
| post | 0.3 | − | 1.452 | + | 0.491 | + |
| 35097 post | 1.5 | + | 3.226 | + | 2.026 | + |
| 35098 post | 1.5 | + | 3.441 | + | 1.908 | + |
| Isolate specific | | | | | | |
| Bucyrus | 3.1 | − | 3.249 | + | 1.110 | + |
| 84-KY-Al | 2.5 | − | 0.888 | − | 0.288 | − |
| Wroclaw-2 | 2.2 | + | 0.424 | + | 0.276 | − |
| Arvac | 2.5 | − | 0.422 | + | 0.319 | + |
| Killed Bucyrus | 1.9 | − | 1.117 | + | 0.620 | + |

$^a$ Log$_{10}$ VN antibody titre ≥ 0.6 is deemed seropositive in the EAV VN neutralising test
$^b$ the cut off value to determine seropositive status was taken as (mean +2SD) of the 8 VN negative control sera (positive ≥ 0.177)
$^c$ the cut off value to determine seropositive status was taken as (mean + 2SD) of the 8 VN negative control sera (positive ≥ 0.308)
pre = pre-vaccination serum sample
post = post-vaccination serum sample

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 12687 base pairs
        (B) TYPE: nucleic acid
        (C) STRANDEDNESS: single
        (D) TOPOLOGY: linear (ii) MOLECULE TYPE: cDNA -continued (xi) SEQUENCE DESCRIPTION: SEQ ID NO: 1:

```
TGCCATATAC GGCTCACCAC CATATACACT GCAAGAATTA CTATTCTTGT GGGCCCCTCT      60
CGGTAAATCC TAGAGGGCTT TCCTCTCGTT ATTGCGAGAT TCGTCGTTAG ATAACGGCAA     120
GTTCCCTTTC TTACTATCCT ATTTTCATCT TGTGGCTTGA CGGGTCACTG CCATCGTCGT     180
CGATCTCTAT CAACTACCCT TGCGACTATG GCAACCTTCT CCGCTACTGG ATTTGGAGGG     240
AGTTTTGTTA GGGACTGGTC CCTGGACTTA CCCGACGCTT GTGAGCATGG CGCGGGATTG     300
TGCTGCGAAG TGGACGGCTC CACCTTATGC GCCGAGTGTT TCGCGGTTG CGAAGGAATG      360
GAGCAATGTC CTGGCTTGTT CATGGGACTG TTAAAACTGG CTTCGCCAGT TCCAGTGGGA     420
CATAAGTTCC TGATTGGTTG GTATCGAGCT GCCAAAGTCA CCGGGCGTTA CAATTTCCTT     480
GAGCTGTTGC AACACCCTGC TTTCGCCCAG CTGCGTGTGG TTGATGCTAG GTTAGCCATT     540
GAAGAGGCAA GTGTGTTTAT TTCCACTGAC CACGCGTCTG CTAAGCGTTT CCCTGGCGCT     600
AGATTTGCGC TGACACCGGT GTATGCTAAC GCTTGGGTTG TGAGCCCGGC TGCTAACAGT     660
TTGATAGTGA CCACTGACCA GGAACAAGAT GGGTTCTGCT GGTTAAAACT TTTGCCACCT     720
GACCGCCGTG AGGCTGGTTT GCGGTTGTAT TACAACCATT ACCGCGAACA AAGGACCGGG     780
TGGCTGTCTA AAACAGGACT TCGCTTATGG CTTGGAGACC TGGGTTTGGG CATCAATGCG     840
AGCTCTGGAG GGCTGAAATT CCACATTATG AGGGGTTCGC CTCAGCGAGC TTGGCATATC     900
ACAACACGCA GCTGCAAGCT GAAGAGCTAC TACGTTTGTG ACATCTCTGA AGCAGACTGG     960
TCCTGTTTGC CTGCTGGCAA CTACGGCGGC TACAATCCAC CAGGGGACGG AGCTTGCGGT    1020
TACAGGTGCT TGGCCTTCAT GAATGGCGCC ACTGTTGTGT CGGCTGGTTG CAGTTCTGAC    1080
TTGTGGTGTG ATGATGAGTT GGCTTATCGA GTCTTTCAAT TGTCACCCAC GTTCACGGTT    1140
ACCATCCCAG GTGGGCGAGT TTGTCCGAAT GCCAAGTACG CAATGATTTG TGACAAGCAG    1200
CACTGGCGCG TCAAACGTGC AAAGGGCGTC GGCCTGTGTC TCGATGAAAG CTGTTTCAGG    1260
GGCATCTGCA ATTGCCAACG CATGAGTGGA CCACCACCTG CACCCGTGTC AGCCGCCGTG    1320
TTAGATCACA TACTGGAGGC GGCGACGTTT GGCAACGTTC GCGTGGTTAC ACCTGAAGGG    1380
CAGCCACGCC CCGTACCAGC GCCGCGAGTT CGTCCCAGCG CCAACTCTTC TGGAGATGTC    1440
AAAGATCCGG CGCCCGTTCC GCCAGTACCA AAACCAAGGA CCAAGCTTGC CACACCGAAC    1500
CCAACTCAGG CGCCCATCCC AGCACCGCGC ACGCGACTTC AAGGGGCCTC AACACAGGAG    1560
CCACTGGCGA GTGCAGGAGT TGCTTCTGAC TCGGCACCTA AATGGCGTGT GGCCAAAACT    1620
GTGTACAGCT CCGCGGAGCG CTTTCGGACC GAACTGGTAC AACGTGCTCG GTCCGTTGGG    1680
GACGTTCTTG TTCAAGCGCT ACCGCTCAAA ACCCCAGCAG TGCAGCGGTA TACCATGACT    1740
CTGAAGATGA TGCGTTCACG CTTCAGTTGG CACTGCGACG TGTGGTACCC TTTGGCTGTA    1800
ATCGCTTGTT TGCTCCCTAT ATGGCCATCT CTTGCTTTGC TCCTTAGCTT TGCCATTGGG    1860
TTGATACCCA GTGTGGGCAA TAATGTTGTT CTGACAGCGC TTCTGGTTTC ATCAGCTAAT    1920
TATGTTGCGT CAATGGACCA TCAATGTGAA GGTGCGGCTT GCTTAGCCTT GCTGGAAGAA    1980
GAACACTATT ATAGAGCGGT CCGTTGGCGC CCGATTACAG GCGCGCTGTC GCTTGTGCTC    2040
AATTTACTGG GGCAGGTAGG CTATGTAGCT CGTTCCACCT TGATGCAGC TTATGTTCCT     2100
TGCACTGTGT TCGATCTTTG CAGCTTTGCT ATTCTGTACC TCTGCCGCAA TCGTTGCTGG    2160
AGATGCTTCG GACGCTGTGT GCGAGTTGGG CCTGCCACGC ATGTTTTGGG CTCCACCGGG    2220
CAACGAGTTT CCAAACTGGC GCTCATTGAT TTGTGTGACC ACTTTTCAAA GCCCACCATC    2280
GATGTTGTGG GCATGGCAAC TGGTTGGAGC GGATGTTACA CAGGAACCGC CGCAATGGAG    2340
```

-continued

```
CGTCAGTGTG CCTCTACGGT GGACCCTCAC TCGTTCGACC AGAAGAAGGC AGGAGCGACT   2400

GTTTACCTCA CCCCCCCTGT CAACAGCGGG TCAGCGCTGC AGTGCCTCAA TGTCATGTGG   2460

AAGCGACCAA TTGGGTCCAC TGTCCTTGGG AACAAACAG GAGCTGTTGT GACGGCGGTC    2520

AAGAGTATCT CTTTCTCACC TCCCTGCTGC GTCTCTACCA CTTTGCCCAC CCGACCCGGT   2580

GTGACCGTTG TCGACCATGC TCTTTACAAC CGGTTGACTG CTTCAGGGGT CGATCCCGCT   2640

TTATTGCGTG TTGGGCAAGG TGATTTTCTA AAACTTAATC CGGGGTTCCG GCTGATAGGT   2700

GGATGGATTT ATGGGATATG CTATTTTGTG TTGGTGGTTG TGTCAACTTT TACCTGCTTA   2760

CCTATCAAAT GTGGCATTGG CACCCGCGAC CCTTTCTGCC GCAGAGTGTT TTCTGTACCC   2820

GTCACCAAGA CCCAAGAGCA CTGCCATGCT GGAATGTGTG CTAGCGCTGA AGGCATCTCT   2880

CTGGACTCTC TGGGGTTAAC TCAGTTACAA AGTTACTGGA TCGCAGCCGT CACTAGCGGA   2940

TTAGTGATCT TGTTGGTCTG CCACCGCCTG GCCATCAGCG CCTTGGACTT GTTGACTCTA   3000

GCTTCCCCTT TAGTGTTGCT TGTGTTCCCT TGGGCATCTG TGGGGCTTTT ACTTGCTTGC   3060

AGTCTCGCTG GTGCTGCTGT GAAAATACAG TTGTTGGCGA CGCTTTTTGT GAATCTGTTC   3120

TTTCCCCAAG CTACCCTTGT CACTATGGGA TACTGGGCGT GCGTGGCGGC TTTGGCCGTT   3180

TACAGTTTGA TGGGCTTGCG AGTGAAAGTG AATGTGCCCA TGTGTGTGAC ACCTGCCCAT   3240

TTTCTGCTGC TGGCGAGGTC AGCTGGACAG TCAAGAGAGC AGATGCTCCG GGTCAGCGCT   3300

GCTGCCCCCA CCAATTCACT GCTTGGAGTG GCTCGTGATT GTTATGTCAC AGGCACAACT   3360

CGGCTGTACA TACCCAAGGA AGGCGGGATG GTGTTTGAAG GGCTATTCAG GTCACCGAAG   3420

GCGCGCGGCA ACGTCGGCTT CGTGGCTGGT AGCAGCTACG GCACAGGGTC AGTGTGGACC   3480

AGGAACAACG AGGTCGTCGT ACTGACAGCG TCACACGTGG TTGGCCGCGC TAACATGGCC   3540

ACTCTGAAGA TCGGTGACGC AATGCTGACT CTGACTTTCA AAAAGAATGG CGACTTCGCC   3600

GAGGCAGTGA CGACACAGTC CGAGCTCCCA GGCAATTGGC CACAGTTGCA TTTCGCCCAA   3660

CCAACAACCG GGCCCGCTTC ATGGTGCACT GCCACAGGAG ATGAAGAAGG CTTGCTCAGT   3720

GGCGAGGTTT GTCTGGCGTG GACTACTAGT GGCGACTCTG GATCTGCAGT GGTTCAGGGT   3780

GACGCTGTGG TAGGGGTCCA CACCGGTTCG AACACAAGTG GTGTTGCCTA CGTGACCACC   3840

CCAAGCGGAA AACTCCTTGG CGCCGACACC GTGACTTTGT CATCACTGTC AAAGCATTTC   3900

ACAGGCCCTT TGACATCAAT CCCGAAGGAC ATCCCTGACA ACATTATTGC CGATGTTGAT   3960

GCTGTTCCTC GTTCTCTGGC CATGCTGATT GATGGCTTAT CCAATAGAGA GAGCAGCCTT   4020

TCTGGACCTC AGTTGTTGTT AATTGCTTGT TTTATGTGGT CTTATCTTAA CCAACCTGCT   4080

TACTTGCCTT ATGTGCTGGG CTTCTTTGCC GCTAACTTCT TCCTGCCAAA AAGTGTTGGC   4140

CGCCCTGTGG TCACTGGGCT TCTATGGTTG TGCTGCCTCT TCACACCGCT TTCCATGCGC   4200

TTGTGCTTGT TCCATCTGGT CTGTGCTACC GTCACGGGAA ACGTGATATC TTTGTGGTTC   4260

TACATCACTG CCGCTGGCAC GTCTTACCTT TCTGAGATGT GGTTCGGAGG CTATCCCACC   4320

ATGTTGTTTG TGCCACGGTT CCTAGTGTAC CAGTTCCCCG GCTGGGCTAT TGGCACAGTA   4380

CTAGCGGTAT GCAGCATCAC CATGCTGGCT GCTGCCCTCG GTCACACCCT GTTACTGGAT   4440

GTGTTCTCCG CCTCAGGTCG CTTTGACAGG ACTTTCATGA TGAAATACTT CCTGGAGGGA   4500

GGAGTGAAAG AGAGTGTCAC CGCCTCAGTC ACCCGCGCTT ATGGCAAACC AATTACCCAG   4560

GAGAGTCTCA CTGCAACATT AGCTGCCCTC ACTGATGATG ACTTCCAATT CCTCTCTGAT   4620

GTGCTTGACT GTCGGGCCGT CCGATCGGCA ATGAATCTCG GTGCCGCTCT CACAAGTTTT   4680

CAAGTGGCGC AGTATCGTAA CATCCTTAAT GCATCCTTGC AAGTCGATCG TGACGCTGCT   4740
```

```
CGTAGTCGCA GACTAATGGC AAAACTGGCT GATTTTGCGG TTGAACAAGA AGTAACAGCT      4800

GGAGACCGTG TTGTGGTTAT CGACGGTCTG GACCGCATGG CTCACTTCAA AGACGATTTG      4860

GTGCTGGTTC CTTTGACCAC CAAAGTAGTA GGCGGTTCTA GGTGCACCAT TTGTGACGTC      4920

GTTAAGGAAG AAGCCAATGA CACCCCAGTT AAGCCAATGC CCAGCAGGAG ACGCCGCAAG      4980

GGCCTGCCTA AAGGTGCTCA GTTGGAGTGG GACCGTCACC AGGAAGAGAA GAGGAACGCC      5040

GGTGATGATG ATTTTGCGGT CTCGAATGAT TATGTCAAGA GAGTGCCAAA GTACTGGGAT      5100

CCCAGCGACA CCCGAGGCAC GACAGTGAAA ATCGCCGGCA CTACCTATCA GAAAGTGGTT      5160

GACTATTCAG GCAATGTGCA TTACGTGGAG CATCAGGAAG ATCTGCTAGA CTACGTGCTG      5220

GGCAAGGGGA GCTATGAAGG CCTAGATCAG GACAAAGTGT TGGACCTCAC AAACATGCTT      5280

AAAGTGGACC CCACGGAGCT CTCCTCCAAA GACAAAGCCA AGGCGCGTCA CGTTGCTCAT      5340

CTGCTGTTGG ATCGGCTAAA CCCAGTTGAG GCAGTGAATC AGTTAAACTG AGAGCGCCCC      5400

ACATCTTTCC CGGCGATGTG GGGCGTCGGA CCTTTGCTGA CTCTAAAGAC AAGGGTTTCG      5460

TGGCTCTACA CAGTCGCACA ATGTTTTTAG CTGCCCGGGA CTTTTTATTT AACATCAAAT      5520

TTGTGTGCGA CGAAGAGTTC ACAAAGACCC CAAAAGACAC ACTGCTTGGG TACGTACGCG      5580

CCTGCCCTGG TTACTGGTTT ATTTTCCGTC GTACGCACCG GTCGCTGATT GATGCATACT      5640

GGGACAGTAT GGAGTGCGTT TACGCGCTTC CCACCATATC TGATTTTGAT GTGAGCCCAG      5700

GTGACGTCGC AGTGACGGGC GAGCGATGGG ATTTTGAATC TCCCGGAGGA GGCCGTGCAA      5760

AACGTCTCAC AGCTGATCTG GTGCACGCTT TTCAAGGGTT CCACGGAGCC TCTTATTCCT      5820

ATGATGACAA GGTGGCAGCT GCTGTCAGTG GTGACCCGTA TCGGTCGGAC GGCGTCTTGT      5880

ATAACACCCG TTGGGCAAC ATTCCATATT CTGTCCCAAC CAATGCTTTG GAAGCCACAG       5940

CTTGCTACCG TGCTGGATGT GAGGCCGTTA CCGACGGGAC CAACGTCATC GCAACAATTG      6000

GGCCCTTCCC GGAGCAACAA CCCATACCGG ACATCCCAAA GAGCGTGCTT GACAACTGCG      6060

CTGACATCAG CTGTGACGCT TTCATAGCGC CCGCTGCAGA GACAGCCCTG TGTGGAGATT      6120

TAGAGAAATA CAACCTATCC ACGCAGGGTT TTGTGTTGCC TAGTGTTTTC TCCATGGTGC      6180

GGGCGTACTT AAAAGAGGAG ATTGGAGACG CTCCACCACT CTACTTGCCA TCTACTGTAC      6240

CATCTAAAAA TTCACAAGCC GGAATTAACG GCGCTGAGTT TCCTACAAAG TCTTTACAGA      6300

GCTACTGTTT GATTGATGAC ATGGTGTCAC AGTCCATGAA AAGCAATCTA CAAACCGCCA      6360

CCATGGCGAC TTGTAAACGG CAATACTGTT CCAAATACAA GATTAGGAGC ATTCTGGGCA      6420

CCAACAATTA CATTGGCCTA GGTTTGCGTG CCTGCCTTTC GGGGGTTACG GCCGCATTCC      6480

AAAAAGCTGG AAAGGATGGG TCACCGATTT ATTTGGGCAA GTCAAAATTC GACCCGATAC      6540

CAGCTCCTGA CAAGTACTGC CTTGAAACAG ACCTGGAGAG TTGTGATCGC TCCACCCCGG      6600

CTTTGGTGCG TTGGTTCGCT ACTAATCTTA TTTTTGAGCT AGCTGGCCAG CCCGAGTTGG      6660

TGCACAGCTA CGTGTTGAAT TGCTGTCACG ATCTAGTTGT GGCGGGTAGT GTAGCATTCA      6720

CCAAACGCGG GGGTTTGTCA TCTGGAGACC CTATCACTTC CATTTCCAAT ACCATCTATT      6780

CATTGGTGCT GTACACCCAG CACATGTTGC TATGTGGACT TGAAGGCTAT TTCCCAGAGA      6840

TTGCAGAAAA ATATCTTGAT GGCAGCCTGG AGCTGCGGGA CATGTTCAAG TACGTTCGAG      6900

TGTACATCTA CTCGGACGAT GTGGTTCTAA CCACACCCAA CCAGCATTAC GCGGCCAGCT      6960

TTGACCGCTG GGTCCCCCAC CTGCAGGCGC TGCTAGGTTT CAAGGTTGAC CCAAAGAAAA      7020

CTGTGAACAC CAGCTCCCCT TCCTTTTTGG CTGCCGGTT CAAGCAAGTG ACGGCAAGT       7080

GTTATCTAGC CAGTCTTCAG GACCGCGTTA CACGCTCTCT GTTATACCAC ATTGGTGCAA      7140
```

```
AGAATCCCTC AGAGTACTAT GAAGCTGCTG TTTCCATCTT TAAGGACTCC ATTATCTGCT    7200

GTGATGAAGA CTGGTGGACG GACCTCCATC GACGTATCAG TGGCGCTGCG CGTACCGACG    7260

GAGTTGAGTT CCCCACCATT GAAATGTTAA CATCCTTCCG CACCAAGCAG TATGAGAGTG    7320

CCGTGTGCAC AGTTTGTGGG GCCGCCCCCG TGGCCAAGTC TGCTTGTGGA GGGTGGTTCT    7380

GTGGCAATTG TGTCCCGTAC CACGCGGGTC ATTGTCACAC AACCTCGCTC TTCGCCAACT    7440

GCGGGCACGA CATCATGTAC CGCTCCACTT ACTGCACAAT GTGTGAGGGT TCCCCAAAAC    7500

AGATGGTACC AAAAGTGCCT CACCCGATCC TGGATCATTT GCTGTGCCAC ATTGATTACG    7560

GCAGTAAAGA GGAACTAACT CTGGTAGTGG CGGATGGTCG AACAACATCA CCGCCCGGGC    7620

GCTACAAAGT GGGTCACAAG GTAGTCGCCG TGGTTGCAGA TGTGGGAGGC AACATTGTGT    7680

TTGGGTGCGG TCCTGGATCA CACATCGCAG TACCACTTCA GGATACGCTC AAGGGCGTGG    7740

TGGTGAATAA AGCTCTGAAG AACGCCGCCG CCTCTGAGTA CGTGGAAGGA CCCCCTGGGA    7800

GTGGGAAGAC TTTTCACCTG GTCAAAGATG TGCTAGCCGT GGTCGGTAGC GCGACCTTGG    7860

TTGTGCCCAC CCACGCGTCC ATGCTGGACT GCATCAACAA GCTCAAACAA GCGGGCGCCG    7920

ATCCATACTT TGTGGTGCCC AAGTATACAG TTCTTGACTT TCCCCGGCCT GGCAGTGGAA    7980

ACATCACAGT GCGACTGCCA CAGGTCGGAA CCAGTGAGGG AGAAACCTTT GTGGATGAGG    8040

TGGCCTACTT CTCACCAGTG GATCTGGCGC GCATTTTAAC CCAGGGTCGA GTCAAGGGTT    8100

ACGGTGATTT AAATCAGCTC GGGTGCGTCG GACCCGCGAG CGTGCCACGT AACCTTTGGC    8160

TCCGACATTT TGTCAGCCTG GAGCCCTTGC GAGTGTGCCA TCGATTCGGC GCTGCTGTGT    8220

GTGATTTGAT CAAGGGCATT TATCCTTATT ATGAGCCAGC TCCACATACC ACTAAAGTGG    8280

TGTTTGTGCC AAATCCAGAC TTTGAGAAAG GTGTAGTCAT CACCGCCTAC CACAAAGATC    8340

GCGGTCTTGG TCACCGCACA ATTGATTCAA TTCAAGGCTG TACATTCCCT GTTGTGACTC    8400

TTCGACTGCC CACACCCCAA TCACTGACGC GCCCGCGCGC AGTTGTGGCG GTTACTAGGG    8460

CGTCTCAGGA ATTATACATC TACGACCCCT TGATCAGCT TAGCGGGTTG TTGAAGTTCA    8520

CCAAGGAAGC AGAGGCGCAG GACTTGATCC ATGGCCCACC TACAGCATGC CACCTGGGCC    8580

AAGAAATTGA CCTTTGGTCC AATGAGGGCC TCGAATATTA CAAGGAAGTC AACCTGCTGT    8640

ACACACACGT CCCCATCAAG GATGGTGTAA TACACAGTTA CCCTAATTGT GGCCCTGCCT    8700

GTGGCTGGGA AAAGCAATCC AACAAAATTT CGTGCCTCCC GAGAGTGGCA CAAAATTTGG    8760

GCTACCACTA TTCCCCAGAC TTACCAGGAT TTTGCCCCAT ACCAAAAGAA CTCGCTGAGC    8820

ATTGGCCCGT AGTGTCCAAT GATAGATACC CGAATTGCTT GCAAATTACC TTACAGCAAG    8880

TATGTGAACT CAGTAAACCG TGCTCAGCGG GCTATATGGT TGGACAATCT GTTTTCGTGC    8940

AGACGCCTGG TGTGACATCT TACTGGCTTA CTGAATGGGT CGACGGCAAA GCGCGTGCTC    9000

TACCAGATTC CTTATTCTCG TCCGGTAGGT TCGAGACTAA CAGCCGCGCT TTCCTCGATG    9060

AAGCCGAGGA AAAGTTTGCC GCCGCTCACC CTCATGCCTG TTTGGGAGAA ATTAATAAGT    9120

CCACCGTGGG AGGATCCCAC TTCATCTTTT CCCAATATTT ACCACCATTG CTACCCGCAG    9180

ACGCTGTTGC CCTGGTAGGT GCTTCATTGG CTGGGAAAGC TGCTAAAGCT GCTTGCAGCG    9240

TTGTTGATGT CTATGCTCCA TCATTTGAAC CTTATCTACA CCCTGAGACA CTGAGTCGCG    9300

TGTACAAGAT TATGATCGAT TTCAAGCCGT GTAGGCTTAT GGTGTGGAGA AACGCGACCT    9360

TTTATGTCCA AGAGGGTGTT GATGCAGTTA CATCAGCACT AGCAGCTGTG TCCAAACTCA    9420

TCAAAGTGCC GGCCAATGAG CCTGTTTCAT TCCATGTGGC ATCAGGGTAC AGAACCAACG    9480

CGCTGGTAGC GCCCCAGGCT AAAATTTCAA TTGGAGCCTA CGCCGCCGAG TGGGCACTGT    9540
```

-continued

```
CAACTGAACC GCCACCTGCT GGTTATGCGA TCGTGCGGCG ATATATTGTA AAGAGGCTCC    9600

TCAGCTCAAC AGAAGTGTTC TTGTGCCGCA GGGGTGTTGT GTCTTCCACC TCAGTGCAGA    9660

CCATTTGTGC ACTAGAGGGA TGTAAACCTC TGTTCAACTT CTTACAAATT GGTTCAGTCA    9720

TTGGGCCCGT GTGATGGGCT TAGTGTGGTC ACTGATTTCA AATTCTATTC AGACTATTAT    9780

TGCTGATTTT GCTATTTCTG TGATTGATGC AGCGCTTTTC TTTCTCATGC TACTTGCATT    9840

GGCTGTTGTT ACTGTGTTTC TTTTCTGGCT CATTGTTGCC ATCGGCCGCA GCTTGGTGGC    9900

GCGGTGTTCA CGAGGTGCGC GTTACAGACC TGTTTAAGGA TTTGCAGTGC GACAACCTGC    9960

GCGCGAAAGA TGCCTTCCCG AGTCTGGGAT ATGCTCTGTC GATTGGCCAG TCGAGGCTAT   10020

CGTATATGCT GCAGGATTGG TTGCTTGCTG CGCACCGCAA GGAAGTTATG CCTTCCAATA   10080

TCATGCCTAT GCCCGGTCTT ACTCCTGATT GCTTTGACCA TCTGGAGTCT TCTAGCTATG   10140

CTCCATTTAT CAATGCCTAT CGGCAGGCAA TTTTGAGTCA ATACCCACAA GAGCTCCAGC   10200

TCGAAGCCAT CAACTGTAAA TTGCTTGCTG TGGTTGCACC GGCATTGTAT CATAATTACC   10260

ATCTAGCCAA TTTGACCGGA CCGGCCACAT GGGTCGTGCC TACAGTGGGC CAGTTGCACT   10320

ATTATGCTTC TTCCTCTATT TTTGCTTCAT CTGTGGAAGT GTTGGCAGCA ATAATACTAC   10380

TATTTGCATG CATACCACTA GTGACACGAG TGTACATCTC TTTTACGCGG CTAATGTCAC   10440

CTTCCCGTCG CACTTCCAGC GGCACTTTGC CGCGGCGCAA GATTTTGTAG TGCACACGGG   10500

TTATGAATAT GCCGGGGTCA CTATGTTAGT GCACTTGTTT GCCAACTTGG TTCTGACATT   10560

TCCGAGCTTA GTTAATTGTT CCCGCCCTGT GAATGTCTTT GCTAATGCTT CTTGCGTGCA   10620

AGTGGTTTGT AGTCATACCA ACTCAACTAC TGGCTTGGGT CAACTTTCTT TTTCCTTTGT   10680

AGATGAAGAT CTACGGCTGC ATATCAGGCC TACTCTTATT TGTTGGTTTG CCTTGTTGTT   10740

GGTGCACTTT CTACCCATGC CACGCTGCAG AGGCTCGTAA TTTTACTTAC ATTAGTCATG   10800

GATTGGGCCA CGTGCACGGT CATGAGGGGT GTAGGAATTT TATTAATGTC ACTCATTCTG   10860

CATTTCTTTA TCTTAATCCC ACCACTCCCA CTGCGCCGGC TATAACTCAT TGTTTACTTC   10920

TGGTTCTGGC AGCCAAAATG GAACACCCAA ACGCTACTAT CTGGCTGCAG CTGCAGCCGT   10980

TTGGGTATCA TGTGGCTGGC GATGTCATTG TCAACTTGGA AGAGGACAAG AGGCATCCTT   11040

ACTTTAAACT TTTGAGAGCG CCGGCTTTAC CGCTTGGTTT TGTGGCTATA GTTTATGTTC   11100

TTTTACGACT GGTACGTTGG GCTCAACGAT GTTATCTATG ATTGTATTGC TATTCTTGCT   11160

TTGGGGTGCG CCATCACATG CTTACTTCTC ATACTACACC GCTCAGCGCT TCACAGACTT   11220

CACCTTGTGT ATGCTGACGG ATCGCGGCGT TATTGCCAAT TTGCTGCGAT ATGATGAGCA   11280

CACTGCTTTG TACAATTGTT CCGCCAGTAA AACCTGTTGG TATTGCACAT TCCTGGACGA   11340

ACAGATTATC ACGTTTGGAA CCGATTGTGA TGACACCTAC GCGGTCCCAG TTGCTGAGGT   11400

CCTGGAACAG GCGCATGGAC CGTACAGTGC GCTGTTTGAT GACATGCCCC CTTTTATTTA   11460

CTATGGCCGT GAATTCGGCA TAGTTGTGTT GGATGTGTTT ATGTTCTATC CGTTTTAGT   11520

TCTGTTTTTC TTATCAGTAC TACCCTATGC TACGCTTATT CTTGAAATGT GTGTATCTAT   11580

TCTGTTTATA ATCTATGGCA TTTACAGCGG GGCCTACTTG GCCATGGGCA TATTTGCGGC   11640

CACGCTTGCT ATACATTCAA TTGTGGTCCT CCGCCAATTA CTGTGGTTAT GCCTGGCTTG   11700

GCGATACCGC TGTACGCTTC ACGCGTCCTT TATATCAGCT GAGGGGAAAG TGTACCCCGT   11760

AGACCCCGGA CTCCCGGTTG CCGCCGTGGG CAATCGGTTG TTAGTCCCAG GTAGGCCCAC   11820

TATCGATTAT GCAGTGGCCT ACGGCAGCAA AGTCAACCTT GTGAGGTTGG GGGCAGCTGA   11880

GGTATGGGAG CCATAGATTC ATTTTGTGGT GACGGGATTT TAGGTGAGTA TCTAGATTAC   11940
```

```
TTTATTCTGT CCGTCCCACT CTTGCTGTTG CTTACTAGGT ATGTAGCATC TGGGTTAGTG    12000

TATGTTTTGA CTGCCTTGTT CTATTCCTTT GTATTAGCAG CTTATATTTG GTTTGTTATA    12060

GTTGGAAGAG CCTTTTCTAC TGCTTATGCT TTTGTGCTTT TGGCTGCTTT TCTGTTATTA    12120

GTAATGAGGA TGATTGTGGG TATGATGCCT CGTCTTCGGT CCATTTTCAA CCATCGCCAA    12180

CTGGTGGTAG CTGATTTTGT GGACACACCT AGTGGACCTG TTCCCATCCC CCGCTCAACT    12240

ACTCAGGTAG TGGTTCGCGG CAACGGGTAC ACCGCAGTTG GTAACAAGCT TGTCGATGGC    12300

GTCAAGACGA TCACGTCCGC AGGCCGCCTC TTTTCGAAAC GGACGGCGGC GACAGCCTAC    12360

AAGCTACAAT GACCTACTGC GCATGTTTGG TCAGATGCGG GTCCGCAAAC CGCCCGCGCA    12420

ACCCACTCAG GCTATTATTG CAGAGCCTGG AGACCTTAGG CATGATTTAA ATCAACAGGA    12480

GCGCGCCACC CTTTCGTCGA ACGTACAACG GTTCTTCATG ATTGGGCATG GTTCACTCAC    12540

TGCAGATGCC GGAGGACTCA CGTACACCGT CAGTTGGGTT CCTACCAAAC AAATCCAGCG    12600

CAAAGTTGCG CCTCCAGCAG GGCCGTAAGA CGTGGATATT CTCCTGTGTG GCGTCATGTT    12660

GAAGTAGTTA TTAGCCACCC AGGAACC                                       12687
```

(2) INFORMATION FOR SEQ ID NO: 2:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

```
Met Ala Ser Arg Arg Ser Arg Pro Gln Ala Ala Ser Phe Arg Asn Gly
 1               5                  10                  15

Arg Arg Arg Gln Pro Thr Ser Tyr Asn Asp Leu Leu Arg Met Phe Gly
            20                  25                  30

Gln Met Arg Val Arg Lys Pro Pro Ala Gln Pro Thr Gln Ala Ile Ile
        35                  40                  45

Ala Glu Pro Gly Asp Leu Arg His Asp Leu Asn Gln Gln Glu Arg Ala
    50                  55                  60

Thr Leu Ser Ser Asn Val Gln Arg Phe Phe Met Ile Gly His Gly Ser
65                  70                  75                  80

Leu Thr Ala Asp Ala Gly Gly Leu Thr Tyr Thr Val Ser Trp Val Pro
                85                  90                  95

Thr Lys Gln Ile Gln Arg Lys Val Ala Pro Ala Gly Pro
            100                 105                 110
```

(2) INFORMATION FOR SEQ ID NO: 3:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Met Ala Ser Arg Arg Ser Arg Pro Gln Ala Ala Ser Phe Arg Asn Gly
 1               5                  10                  15

Arg Arg Arg Gln Pro Thr Ser Tyr Asn Asp Leu Leu Arg Met Phe Gly
            20                  25                  30
```

-continued

```
    Gln Met Arg Val Arg Lys Pro Pro Ala Gln Pro Thr Gln Ala Ile